United States Patent [19]

Nabi et al.

[11] Patent Number: 5,472,684
[45] Date of Patent: Dec. 5, 1995

[54] ORAL COMPOSITIONS FOR PLAQUE AND GINGIVITIS

[75] Inventors: Nuran Nabi, North Brunswick; Abdul Gaffar, Princeton; Shirley Lucchesi, Westfield; John J. Afflitto, Brookside; Susan M. Herles, Flemington, all of N.J.

[73] Assignee: Colgate Palmolive Company, Piscataway, N.J.

[21] Appl. No.: 71,119

[22] Filed: Jun. 2, 1993

[51] Int. Cl.⁶ .................................................. A61K 7/16
[52] U.S. Cl. ........................................................ 424/49
[58] Field of Search ................................................ 424/49

[56] References Cited

U.S. PATENT DOCUMENTS

| | | | |
|---|---|---|---|
| 4,649,044 | 3/1987 | Gomi et al. | 424/49 |
| 4,925,655 | 5/1990 | Smigel et al. | 424/52 |
| 4,962,133 | 10/1990 | Chromecek et al. | 521/56 |
| 5,145,665 | 9/1992 | Klueppel et al. | 424/50 |
| 5,178,869 | 1/1993 | Ebine et al. | 424/401 |
| 5,182,099 | 1/1993 | Jönsson et al. | 424/49 |
| 5,215,748 | 6/1993 | Mankovitz | 424/195.1 |
| 5,256,401 | 10/1993 | Duckenfield et al. | 424/49 |
| 5,296,214 | 3/1994 | Gaffar | 424/49 |

FOREIGN PATENT DOCUMENTS 2445676  4/1976  Germany.

*Primary Examiner*—Peter O'Sullivan
*Attorney, Agent, or Firm*—Robert C. Sullivan; Robert L. Stone; Murray M. Grill

[57] ABSTRACT

A composition comprising thymol and eugenol, and optionally a sesquiterpene alcohol, such as, farnesol or has been found to have plaque and gingivitis effect. Flavoring agents may be included to provide an organoleptically acceptable oral product. Australian Tea Tree oil, sage oil and eucalyptol were found to enhance the antiplaque and antigingivitis activity of mouthrinses formulated from these compositions.

These compositions exhibit an antibacterial effect vs. *A. viscosus* of about 25 MIC or less.

19 Claims, No Drawings

ORAL COMPOSITIONS FOR PLAQUE AND GINGIVITIS

This invention relates to a composition effective in countering plaque and gingivitis and more particularly to a combination of natural flavoring agents having an effect on plaque and gingivitis.

BACKGROUND OF THE INVENTION

The use of natural products in medicated lotions for the treatment of teeth and gums is old in the art having been practiced and documented since 1860 when U.S. Pat. No. 30,834 was granted for medicated lotions containing natural product extracts from cloves and myrrh to J. G. Popp. Since then, many patents have disclosed the compositions of oral products containing natural product extracts. For example, U.S. Pat. No. 69,388 was issued to C. E. Blake for a tooth powder flavored with rose, bergamot or winter-green. U.S. Pat. No. 115,719 was issued to J. O. Draper for a tooth soap containing tincture of myrrh and pulverized orris root. However, none of the prior art references disclosed clinically proved records for plaque and gingivitis effect in humans.

Bacterial plaque on tooth surfaces is a major etiological factor in gingivitis and periodontitis as shown by M. M. Ash et al., J. Peridontal, 35:424–429, 1964; H. Leo et al. J. Periodontal 36:177–187, 1965; and E. Theilade et al., J. Peridont Res. 1:1–13, 1966. Recently, specific oral microorganisms in plaque have been implicated in chronic periodontal disease. One approach to mitigate developing gingivitis and periodontitis is to prevent or reduce plaque formation. There is also evidence that antibacterials can be beneficial as an adjunct to the mechanical removal of plaque. Moreover, it has been shown recently that a toothpaste and a mouthrinse composition containing an antibacterial chemical, commercially known as Triclosan, reduce plaque and gingivitis in clinical studies in humans.

It is an object of this invention to provide improved oral compositions, such as, toothpastes and mouthrinses.

It is another object to provide improved oral compositions containing a combination of natural flavoring agents.

Other objects will become apparent to those skilled in the art upon a further reading of the specification.

SUMMARY OF THE INVENTION

It has now been found that a composition comprising a combination of thymol and eugenol or of thymol, eugenol and a sesquiterpene alcohol in an organoleptically acceptable oral product, such as, a toothpaste or mouthrinse provides plaque and gingivitis effect in humans. Exemplary sesquiterpene alcohols include farnesol, nerolidol, bisabolol, santolol, and the like. Flavoring agents, such as chammomile tincture, myrrh gum tincture, rhatany root, Australian Tree oil, eucalyptol, sage oil and the like can also be added to improve the taste and in the case in which one or more of Australian Tea Tree oil, eucalyptol and sage oil are used, enhance the plaque and gingivitis effect of thymol and eugenol and thymol, eugenol, sesquiterpene alcohol oral compositions.

DESCRIPTION OF THE INVENTION

The amounts of thymol, eugenol and optionally sesquiterpene alcohol may vary considerably. It is preferred, however, to use at least about 5 parts per million (ppm) based on the total weight of the oral compositions. A particularly useful range, for example in a mouthrinse is about 1,000 to about 20,000 ppm of thymol and about 1,000 to about 20,000 ppm of eugenol particularly if Australian Tea Tree oil is not present. Another particularly useful range in a mouthrinse when Australian Tea Tree oil is employed is about 5 to about 500 ppm of thymol and about 5 to about 500 ppm of eugenol. Australian Tea Tree oil, when employed, is used in an amount of about 50 to about 5,000 ppm in a mouthrinse.

When any of the other flavoring agents enumerated above is employed, a useful range, for instance for eucalyptol, sage oil and the others, lies between about 50 and about 10,000 ppm, preferably up to about 5,000 ppm.

In compositions such as toothpastes, a particularly useful range is about 5,000 to about 20,000 ppm of eugenol when Australian Tea Tree oil is absent. When Australian Tea Tree oil is present, typically amounts of about 500 to about 3,000 ppm of each of thymol and eugenol are used.

When a sesquiterpene alcohol is present, it is typically employed in amounts of about 1,000 to about 20,000 in mouthrinse and about 5,000 to about 20,000 ppm in toothpaste which does not contain Australian Tea Tree oil and about 5 to about 500 ppm in mouthrinse and about 500 to about 3,000 ppm in toothpaste containing Australian Tea Tree oil.

The antiplaque-antigingivitis compositions of this invention may be incorporated into oral formulations in general. In addition to their use in mouthrinses and toothpastes, they be used in lozenges, chewing gum or dental floss containing a dental vehicle.

The dental vehicle contains liquids and solids in a dentifrice. In general, the liquid comprises water and/or a humectant, such as, glycerine, sorbitol, polyethylene glycol or propylene glycol including suitable mixtures thereof. It is usually advantageous to use a mixture of both water and one or more humectants. The total liquid content is generally about 5–90 percent by weight of the vehicle. In transparent and translucent vehicles, the liquid content of the toothpaste may be about 5–90 percent by weight, while in opaque vehicles the total liquid content is usually about 5–50 percent by weight. The preferred humectants are glycerine, sorbitol, and polyethylene glycol.

The solid portion of the vehicle is a gelling agent. In the instant invention, the gelling agent includes alkali metal carboxymethyl cellulose, hydroxyethyl cellulose, and hydroxymethyl cellulose in an amount of at least about 0.5 percent by weight of the vehicle. Additional gelling agents may also be present. Gelling agents which may be additionally present include xanthan gum, viscarin, gelatin, starch, glucose, sucrose, polyvinyl pyrrolidone, polyvinyl alcohol, gum tragacanth, gum karaya, hydroxypropyl cellulose, methyl cellulose, carboxyethyl cellulose (CMC), and sodium alginate. Laponite CP or SP, which are each synthetic inorganic complex silicate clays, are sold under trademark by Laporte Industries, LTD. and magnesium aluminum silicate gel. The solid portion or gelling agent of the vehicle is typically present on an amount of about 0.5–5.0 percent by weight of the toothpaste and preferably about 0.5–2.0 percent by weight.

Any suitable substantially water-insoluble polishing agent may be added to the gel vehicle of the dentifrice. There is a relatively large number of such materials known in the art. Representative materials include, for example, dicalcium phosphate, tricalcium phosphate, aluminum hydroxide, magnesium carbonate, calcium carbonate, calcium pyrophosphate, calcium sulfate, bentonite, alumina, hydrated alumina, aluminum silicate, zirconium silicate, silica, including mixtures thereof.

Water-soluble polishing agents, such as sodium bicarbonate can also be used. When sodium bicarbonate is present, plaque and caries reduction is improved in accordance with the present invention.

In general these polishing agents will comprise a major proportion by weight of the solid ingredients. The polishing agent content is variable but will generally be up to about 75 percent by weight of the total composition, preferably about 20–75 percent, although even lower amounts of polishing agent can be employed, for instance about 10% or more of sodium bicarbonate.

Any suitable surface-active material may be incorporated into the gel vehicle. Such compatible materials are desirable to provide detersive and foaming properties depending upon the specific type of surface-active material selected. These detergents are water-soluble organic compounds for the most part and may be anionic, cationic or non-ionic in structure. It is preferred to use the water-soluble non-soap or synthetic organic detergents. Suitable detersive materials are known and include the water-soluble anionic salts of higher fatty acid monoglyceride monosulfate detergents (e.g., sodium coconut fatty acid monoglyceride monosulfate), higher alkyl sulfates (e.g., sodium lauryl sulfate), alkyl aryl sulfonates (e.g., sodium dodecyl benzene sulfonate), higher fatty acid esters of 1,2-dihydroxypropane sulfonate, and the like. Other suitable surface-active materials include non-ionic surface-active agents, such as condensates of ethylene oxide with propylene oxide condensates of propylene glycol (Pluronics).

The various surface-active materials may be used in any suitable amount, generally from about 0.05 to about 10 percent by weight, and preferably from about 0.5 to about 5 percent by weight of the dentifrice composition.

The oral products of the present invention may also contain antiplaque activity boosters in minimal amounts up to about 5 percent by weight, such as polyvinyl maleic acid/maleic anhydride copolymer or polyvinyl phosphonate which deposits on tooth surfaces and inhibits plaque adhesion onto the surface. Thymol, eugenol, and sesquiterpene alcohols work by a different mechanism, viz., as antimicrobials they inhibit bacterial reproduction and hence plaque growth. Therefore, the two different mechanisms for fighting plaque are complimentary, showing an additive or even synergistic effect.

The oral products of this invention may also contain conventional ingredients, such as coloring or whitening agents (e.g., titanium dioxide), flavoring and/or sweetening materials, fluorides, such as sodium fluoride, stannous fluoride, and sodium monofluorophosphate, and the like. These additional ingredients may each be added to the dentifrice in minimal amounts of up to 5 percent by weight and preferably up to about 1 percent, with respect to compounds which do not contain fluorine and with respect to compounds which do contain fluorine, amounts to provide about 100 to about 10,000 ppm fluoride, preferably about 500 to about 2,000 ppm, provided that they do not interfere with the antiplaque properties of the finished product.

The oral product may also be a liquid, such as mouthrinse which typically contains about 60–99 percent by weight of an aqueous non-toxic lower aliphatic alcohol, preferably having about 5–30 percent by weight of a non-toxic alcohol, such as ethanol, n-propanol, or isopropanol, with water and often about 5–35 percent of humectant.

Such oral preparations are typically applied by contacting natural or artificial teeth and gums through brushing with a dentifrice or toothpaste or by contacting teeth and gums by rinsing the oral cavity for about 15–90 seconds, or in the case where lozenges, candy or chewing gum are used by sucking or chewing in the oral cavity, or in the case of a mouthspray by spraying the oral surfaces at least once daily.

The invention is further described in the examples which follow. All parts and percentages are by weight unless otherwise specified.

EXAMPLE 1

Antibacterial Activity of Natural Flavoring Agents Against Dental Plaque Bacteria The antibacterial activities of a number of natural flavoring agents were evaluated against *Actinomyces viscosus*, a dental plaque bacterium, by measuring the minimum inhibitory concentration (hereinafter referred to as MIC) of the respective agents in vitro according to the standard serial dilution method delineated in N. Nabi et al., Am. J. Dent. 2: 197:206, 1989 which is incorporated herein by reference. The MIC is defined for the purpose of this invention to mean the concentration of a particular agent at which no bacterial growth was observed. The natural flavoring agents used were obtained from commercial sources available in organic or aqueous solvents. The antibacterial compound, Triclosan, was used as a positive Control. Triclosan is 2,4,4'-trichloro-2'-hydroxydiphenyl ether.

The results of the evaluation are presented in Table 1. These data show that among all the agents tested, thymol, eugenol and farnesol are most active against the dental plaque bacterium, *A. viscosus*. These data further show that a combination of thymol/eugenol and thymol/eugenol/farnesol provides more antibacterial activity against *A. viscosus* than the individual component. This suggest a synergistic effect by the combination. Surprisingly, chammomile, rhatany root and myrrh gum alone or in combination although far less effective than thymol, eugenol or farnesol do not enhance or inhibit the antibacterial activity of thymol, eugenol or farnesol. On the basis of these results, oral products, such as, toothpaste or mouthrinse have been formulated based on thymol and eugenol with optional amounts of chammomile, myrrh gum and rhatany root extracts for taste. Australian Tea Tree oil was also used as an optional component for taste and efficacy improvement. Eucalyptol and sage oil also improve taste and efficacy. Farnesol may also be present (although it may detract from the taste perception) since it evinced excellent antibacterial activity equivalent to thymol or eugenol.

TABLE 1

| Agents | Antibacterial Activity vs. *A. viscosus* MIC (ppm) |
| --- | --- |
| Thymol | 25.0 |
| Eugenol | 25.0 |
| Thymol/Eugenol | 12.5 |
| Thymol/Eugenol/Farnesol | 12.5 |
| Chammomile | >100.0 |
| Rhatany root | >100.0 |
| Myrrh Gum | >100.0 |
| Chammomile/Rhatany root/Myrrh gum | >100.0 |
| Eugenol/Chammomile/Rhatany root/Myrrh Gum | 25.0 |
| Thymol/Eugenol/Farnesol/Chammomile/Myrrh Gum/Rhatany root | 12.5 |

TABLE 1-continued

| Agents | Antibacterial Activity vs. *A. viscosus* MIC (ppm) |
|---|---|
| Thymol/Eugenol/Farnesol/Chammomile/ Myrrh Gum/Rhatany root | 12.5 |
| Farnesol | 25.0 |
| Eichanecea | 100.0 |
| Australian Tea Tree Oil | 100.0 |
| Oil of Tulsi | 100.0 |
| Neem Oil | 100.0 |
| Goldenseal | 100.0 |
| Sunphenon Tea Extracts | >100.0 |
| Marigold | >100.0 |
| Pyncnogenol | 100.0 |
| Triclosan | 5.0 |

EXAMPLE 2

Mouthrinse and Dentifrice Compositions Containing Natural Flavoring Agents/Products Mouthrinse and dentifrice were made with natural flavoring agents/products as shown in Tables 2 and 3, respectively. The antiplaque and antigingivitis activities of mouthrinse and dentifrice were evaluated by in vitro and in vivo methods. The results are described in the Examples below.

TABLE 2

Composition of Natural Product Rinse

| Ingredients | Rinse-(1) (Wt. %) | Placebo (Wt. %) |
|---|---|---|
| Water | 68.63 | 69.53 |
| Glycerine | 10.00 | 10.00 |
| Ethanol 95% | 20.00 | 20.00 |
| Thymol 50% | 0.30 | — |
| Eugenol | 0.50 | — |
| Chamomile 46.5% | 0.15 | — |
| Myrrh gum 16.0% | 0.15 | — |
| Rhatany root 57.7% | 0.15 | — |
| Peppermint Flavor Oil | 0.10 | 0.1 |
| Na lauryl sulfate | 0.25 | 0.25 |
| Na Benzoate | 0.1 | 0.1 |
| Na Saccharin | 0.02 | 0.02 |

TABLE 3

Composition of Natural Product Dentifrice

| Ingredients | Dentifrice (1) (Wt. %) | Placebo (Wt. %) |
|---|---|---|
| Water | 27.417 | 27.417 |
| Glycerine | 30.5 | 33.0 |
| Ethanol 95% | 2.0 | 2.0 |
| Zeodent 113 (Silica) | 33.0 | 33.0 |
| Thymol 50% | 1.0 | — |
| Eugenol | 0.50 | — |
| Chamomile 46.5% | 0.50 | — |
| Myrrh gum 16.0% | 0.50 | — |
| Peppermint Flavor oil | 0.89 | 0.89 |
| Na lauryl sulfate | 1.2 | 1.2 |
| Na Benzoate | 0.50 | 0.50 |
| Na Saccharin | 0.20 | 0.20 |
| Na Fluoride | 0.243 | 0.243 |
| Na Carboxymethyl Cellulose | 1.00 | 1.00 |
| Na Pyrophosphate | 0.25 | 0.25 |
| $TiO_2$ | 0.30 | 0.30 |

EXAMPLE 3

In Vitro Antibacterial Activities Of Natural Product Rinse

The antibacterial activity of the natural product rinse vs. placebo against two dental plaque organisms, viz., *A. viscosus* and *Streptococcus sanguis* was evaluated by measuring the minimum inhibitory concentration(MIC) of the rinse presented in Table 2 in vitro. The results delineated in Table 4 show that Natural Product Rinse(1) inhibited the growth of the two dental plaque organisms, *A. viscosus* and *S. sanguis*, and that this inhibitory effect was over and above that of the matching placebo rinse. The antibacterial activity of the rinse was also evaluated by a short interval killing test(SIKT). In this test, 0.1 ml of rinse was mixed with 1.9 ml of *A. viscosus*($10^6$ cell/ml) and incubated at 37° C. for 2 minutes. The incubation was stopped by adding cold Tryptic Soya broth and the viability of the bacteria was measured by growing the organisms on Tryptic Soya agar plates. The % killing of *A. viscosus* was calculated by comparing the colony forming units from the rinse treatment with those of the Control. The results in Table 5 show that 100% Of the *A. viscosus* were killed by the treatment with Natural Product Rinse (1) whereas there was no killing at all from the treatment with the placebo rinse.

TABLE 4

Antibacterial Activity (MIC) of Natural Product Rinse (1) vs. *A. Viscosus* and *S. Sanguis*

| | Minimum Inhibitory Concentration (% Rinse) | |
|---|---|---|
| Rinses | *A. viscosus* | *S. sanguis* |
| Placebo | 20.0 | 8.0 |
| Natural Product Rinse (1) | 8.0 | 2.0 |

TABLE 5

Short Interval Killing Test of Natural Product Rinse (1) Against *A. viscosus*

| Rinses | % Killing |
|---|---|
| Placebo | 0.0 |
| Natural Product Rinse (1) | 100.0 |

EXAMPLE 4

In Vitro Antiplaque Activities of Natural Product Rinse

The in vitro antiplaque activity of Natural Product Rinse (1) was evaluated according to the method described supra in Example 1. Extracted human teeth were cleaned by gentle prophylaxes and autoclaved. They were then treated with a rinse, followed by challenging with a mixture of *A. viscosus* and *Streptococcus mutans* for plaque growth on teeth surfaces. The procedure was repeated for three days. Placebo rinse and sterilized water were used as placebo control and negative control, respectively. The results presented in Table 6 indicated that Natural Product Rinse(1) inhibited plaque formation on tooth surfaces by 39.7% compared with a water control. The placebo rinse inhibited only 5.8% of the plaque formation under similar conditions.

TABLE 6

In Vitro Antiplaque Activity of Natural Product Rinse (1)

| Rinses | Plaque Reduction % |
| --- | --- |
| Water Control | — |
| Natural Product Rinse (1) | 39.7 |
| Placebo | 5.8 |

EXAMPLE 5

Antigingivitis and Antiplaque Activities of Natural Product Rinse in a Clinical Study in Monkeys The efficacy of natural product rinse was evaluated in vivo for reduction of gingivitis and plaque in a clinical study in monkeys. Two groups of monkeys (N=6 in each group) were treated with Natural Product Rinse(1) and placebo rinse for 6 weeks. Gingivitis index and plaque index were scored at initial, 3 weeks and 6 week time points. The results showed that Natural Product Rinse(1) provided 25% reduction in gingivitis after 6 weeks of treatment compared with the placebo (Table 7). There was a 0.2% reduction in plaque score by Natural Product Rinse(1) under similar conditions (Table 8).

TABLE 7

Effect of Natural Product Rinse (1) on Gingivitis in a Clinical Study in Monkeys

| | | Gingivitis Index | | | |
| --- | --- | --- | --- | --- | --- |
| Rinses | N | Init. | 3 Wks | 6 Wks | % Reduction |
| Placebo | 6 | 0.78 | 1.22 | 1.36 | — |
| Nat. Prod. Rinse | 6 | 0.71 | 0.87 | 1.01 | 25.00 |

TABLE 8

Effect of Natural Product Rinse (1) on Plaque in a Clinical Study in Monkeys

| | | Plaque Index | | | |
| --- | --- | --- | --- | --- | --- |
| Rinses | N | Init. | 3 Wks | 6 Wks | % Reduction |
| Placebo | 6 | 1.13 | 1.19 | 1.15 | — |
| Nat. Prod. Rinse | 6 | 1.38 | 1.32 | 1.18 | 0.2 |

EXAMPLE 6

Effect of Natural Product Rinse on Plaque Reduction in a Clinical Study in Humans The efficacy of natural product rinse on the reduction of plaque was evaluated in a clinical study in humans. The study was randomized, blind, 3 cells cross-over design to measure the effects of each rinse on 4 day plaque growth from a zero baseline. Fifteen volunteers rinsed twice daily with each rinse, and plaque was recorded by area and score (Addy et al. J. Clin. Perio. 10, p. 89–99 (1983), Quigley and Hein J.A.D.A. 65, p. 26–29 (1962). Three rinses were used, viz., natural product rinse(1) (test rinse), 0.2% chlorhexidine (positive control) and 0.9% saline (negative control).The mean plaque scores and plaque areas for the respective rinses are shown in Tables 9 and 10 respectively. The results show that Natural Product Rinse(1) inhibited 27.7% and 59.2% regrowth of plaque measured by plaque score and area, respectively after 4 days of treatment compared with 0.9% saline rinse. On the other hand, 0.2% chlorhexidine rinse, clinically proven for plaque and gingivitis effect, inhibited 48.0% and 78.0% regrowth of plaque measured by score and area, respectively under similar conditions.

TABLE 9

Effect of Natural Product Rinse (1) on 4-Day Plaque Regrowth in a Clinical Study in Humans

| Rinses | Plaque Score | Plaque Reduction % |
| --- | --- | --- |
| Saline | 5.30 +/− 0.93 | — |
| Nat. Prod. Rinse (1) | 3.83 +/− 0.79 | 59.2* |
| Chlorhexidine (0.2%) | 0.128 +/− 0.068 | 48.0* |

*p values = <0.001

TABLE 10

Effect of Natural Product Rinse (1) on 4-Day Plaque Regrowth in a Clinical Study in Humans

| Rinses | Plaque Area | Plaque Reduction % |
| --- | --- | --- |
| Saline | 0.31 +/− 0.127 | — |
| Nat. Prod. Rinse (1) | 0.128 +/− 0.068 | 59.2* |
| Chlorhexidine (0.2%) | 0.069 +/− 0.055 | 78.0* |

*p values = <0.001

EXAMPLE 7

Antibacterial Activity of Natural Product Dentifrice(1) Against Dental Plaque Bacteria The antibacterial activity of the natural flavoring agents/products was evaluated in a complete dentifrice product against A. viscosus, a dental plaque bacterium, by determining MIC and SIKT in vitro. The results of both MIC and SIKT show that Natural Product Dentifrice (1) has strong antibacterial activity against dental plaque bacteria, and the antibacterial activities are comparable to gum protection formula (GPF) dentifrices of Colgate-Palmolive Company, a clinically proven antiplaque and antigingivitis dentifrice containing Triclosan, and well and above the matching placebo (Table 11). These results further suggest that antibacterial activities of the natural flavoring agents/products are compatible with the dentifrice ingredients.

TABLE 11

Antibacterial Activities of Natural Product Dentifrice (1) Against A. viscosus

| Dentifrices | SIKT (% Killing) | MIC (% Rinse) |
| --- | --- | --- |
| Placebo | 0.0 | 1.0 |
| GPF | 70.0 | 0.5 |
| Nat. Prod. Dentifrice (1) | 72.3 | 0.5 |

EXAMPLE 8

Optimized Compositions of Mouthrinse and Dentifrice for Improved Taste and Efficacy Since a full patient compliance with an organoleptically acceptable product is a prerequisite for a new product to give clinical effect, the compositions of the mouthrinse and dentifrice were optimized to improve further the taste and efficacy of the product with substantial lowering of the amounts of the antiplaque and antigingivitis components by adding Australian tea tree oil. Improved taste and efficacy are also attained by adding eucalyptol and/or sage oil. The optimized formula of mouthrinse and dentifrice are described in Tables 12 and 16, respectively. The efficacy of the product was evaluated by in vitro methods as shown below in Examples 9 and 10.

TABLE 12

Composition of Natural Product Rinse

| Ingredients | Rinse (2)[a] | Placebo[a] | Rinse (3)[a] |
| --- | --- | --- | --- |
| Glycerine | 10.00 | 10.00 | 10.00 |
| Sorbitol | 10.00 | 10.00 | 10.00 |
| Ethanol 95% | 15.00 | 20.00 | 15.00 |
| Thymol | 0.03 | — | 0.03 |
| Eugenol | 0.03 | — | 0.03 |
| Chamomile 46.5% | 0.05 | — | 0.05 |
| Myrrh gum 16.0% | 0.10 | — | 0.10 |
| Rhatany root 57.7% | 0.05 | — | 0.05 |
| Australian Tea Tree Oil | 0.03 | — | 0.03 |
| Sage Oil | — | — | 0.10 |
| Eucalyptol | — | — | 0.50 |
| Pluronic F-127[b] | 0.05 | 0.15 | 0.05 |
| Flavor oil-peppermint | 0.10 | 0.10 | 0.10 |
| Sodium lauryl sulfate | 0.25 | 0.25 | 0.25 |
| FD & C #40 Dye 1% | 0.015 | 0.015 | 0.015 |
| Water | Q. S. to 100 | Q. S. to 100 | Q. S. to 100 |

[a] = Wt. %
[b] = Trade name for polyoxyethylene-polyoxypropylene block copolymer available from Wyandotte Chem. Co.

EXAMPLE 9

In Vitro Antibacterial Activity of Optimized Natural Product Rinse

The antibacterial activities of the optimized natural product rinse (2) was assessed in vitro by determining MIC and SIKT. The results in Table 13 show that MIC of natural product rinse (2) against four plaque bacteria is lowest compared with Actibrush (with Triclosan) and Listerine (with phenolic flavor), two commercial mouthrinses. These results suggest that natural product rinse (2) is most active against dental plaque bacteria compared to commercial Actibrush and Listerine rinses. The results of SIKT (Table 14) show that natural product rinse (2) kills dental plaque and saliva bacteria in the range of about 89% which is equal to the activity of Actibrush under similar conditions.

TABLE 13

Antibacterial Activity of Natural Product Rinse (2) Against Oral Bacteria

| | Minimum Inhibitory Concentration (% Rinse) | | | |
| --- | --- | --- | --- | --- |
| Rinses | A. viscosus | S. mutans | S. sanguis | P. gingivalis |
| Natural Product Rinse (2) | 1.0 | 1.0 | 1.0 | 1.0 |
| Actibrush | 1.0 | 4.0 | 4.0 | 2.0 |
| Listerine | 16.0 | 19.0 | 19.0 | 19.0 |

TABLE 14

Short Interval Killing Test of Natural Product Rinse (2) Against Oral Bacteria

| | % Killing | | | |
| --- | --- | --- | --- | --- |
| Rinses | A. viscosus | S. mutans | S. sanguis | Total Saliva Bacteria |
| Water Control | — | — | — | — |
| Natural Product Rinse (2) | 89.3 | 92.0 | 99.7 | 99.2 |
| Actibrush | 92.0 | 88.5 | 94.7 | 99.8 |

EXAMPLE 10

In Vitro Plaque Efficacy of Optimized Natural Product Rinse (2) in Flow Cell System The effect of natural product rinse (2) to inhibit bacterial plaque formation in vitro was assessed using the Chemostat Plaque Model according to methods of A. Gaffar et al. described in Am. J. Dent., 3, p. S7–S14, 1990. This in vitro model simulates the actual saliva and tooth surface interactions with respect to the plaque formation in the mouth and assesses the interactions, at biophysical and surface chemical level, of saliva-coated bacteria to saliva-coated surfaces with a surface energy similar to dental enamel. The results presented in Table 15 show that, compared to a matching placebo, natural product rinse (2) was effective in reducing 64% of plaque score, 67% of bacterial mass, 60% of plaque area and 71% of carbohydrate contents. These results, taken together, suggest that optimized natural product rinse (2), not only reduces plaque score, but also the nature of plaque by reducing bacterial mass and carbohydrate contents. It was found that the addition of about 0.5 wt % of eucalyptol or about 0.01 wt. % of sage oil to natural product rinse (2) increases the antiplaque activity assessed by Chemostat Plaque Model in vitro.

TABLE 15

In Vitro Plaque Effect of Natural Product Rinse (2) Evaluated by Artificial Mouth

| Rinse | PS | Bact. | PA | Ex-CHO |
| --- | --- | --- | --- | --- |
| Placebo | 1.0 (0.0) | 1.0 (0.0) | 1.0 (0.0) | 1.0 (0.0) |
| Natural Product Rinse (2) | 0.36 (64.0) | 0.33 (67.0) | 0.40 (60.0) | 0.29 (71.0) |

PS = Plaque Score (% Inhibition)
Bact. = Bacteria (% Inhibition)
PA = Plaque Area (% Inhibition)
Ex-CHO = Carbohydrate (% Inhibition)

EXAMPLE 10

Optimized Natural Product Dentifrices

The compositions set forth in Table 16, containing Australian Tea Tree oil, are optimized for effectiveness with lowered amounts of antiplaque and antigingivitis components.

TABLE 16

Composition of Natural Product Dentifrices

| Ingredients | Dentifrice (2) (Wt. %) | Dentifrice (3) (Wt. %) | Dentifrice (4) (Wt. %) |
|---|---|---|---|
| Water | 24.207 | 26.307 | 18.30 |
| Glycerine | 20.00 | 20.00 | 35.45 |
| Sorbitol | 15.00 | 20.00 | — |
| Zeodent 113 (Silica) | 33.0 | 33.0 | 15.0 |
| Sodium Bicarbonate | — | — | 25.0 |
| Thymol 50% | 0.50 | 0.25 | 0.25 |
| Eugenol | 0.30 | 0.125 | 0.15 |
| Chamomile 46.5% | 0.50 | 0.25 | 0.25 |
| Myrrh gum 16.0% | 1.00 | 0.5 | 0.50 |
| Rhatany root 57.7% | 0.50 | 0.25 | 0.25 |
| Australian Tea Tree Oil | 0.30 | 0.125 | 0.15 |
| Flavor oil-peppermint | 1.1 | 1.1 | 1.1 |
| Sodium lauryl sulfate | 1.5 | 1.5 | 1.5 |
| Na Saccharin | 0.20 | 0.2 | 0.2 |
| Na Fluoride | 0.243 | 0.243 | 0.243 |
| Na Carboxymethyl Cellulose | 1.0 | 1.0 | 1.0 |
| Na pyrophosphate | 0.25 | 0.25 | 0.25 |
| FD & C Dye #40 (1%) | 0.4 | 0.4 | 0.4 |

The compositions of this invention are most effective against plaque and gingivitis within a pH range of about 4 to about 10.5 with a preferred range of about 6 to about 10 and a most preferred range of about 7 to about 10.

Additional natural flavoring agents/products to Australian Tea Tree oil, eucalyptol, sage oil and those earlier discussed can be added without inhibiting the efficacy of the combination of thymol and eugenol or of thymol, eugenol and sesquiterpene alcohol critical to the compositions of this invention. Among the added agents that can be used are: Tulsi oil, Neem oil, Eichinacea tincture, rosemary extracts, goldenseed extracts, passion flower extract, rumeric extracts, betel nut extracts, sunphenon tea extracts, dandelion root extracts, and the like.

Although the invention has been described with a certain amount of particularity, it is understood that the present disclosure of the preferred forms has been made only by way of example and that numerous changes can be resorted to without departing from the spirit and the scope of the invention.

What is claimed is:

1. An oral composition having plaque and gingivitis effect consisting essentially of a combination of thymol and eugenol or thymol, eugenol and a sesquiterpene alcohol.

2. Composition claimed in claim 1 wherein the amount the combination of thymol and eugenol or of thymol, eugenol and sesquiterpene alcohol is at least about 5 ppm of the total composition.

3. Composition claimed in claim 1 wherein the amount of thymol present is about 1,000 ppm to about 20,000 ppm and the amount of eugenol present is about 1,000 ppm to about 20,000 ppm based on the weight of the oral composition and said composition is a mouthrinse.

4. Composition claimed in claim 1 wherein the amount of thymol present is about 5,000 ppm to about 20,000, the amount of eugenol present is about 5,000 ppm to about 20,000 ppm and the amount of sesquiterpene alcohol if present is about 1,000 ppm to about 20,000 ppm based on the weight of the oral composition and said composition is a toothpaste.

5. Composition claimed in claim 1 wherein the sesquiterpene alcohol is present and is farnesol.

6. Composition claimed in claim 1 including a flavoring agent selected from the group consisting of chamomile, myrhh gum, rhatany root, Australian Tea Tree oil, eucalyptol, sage oil and mixtures thereof.

7. Composition claimed in claim 6 wherein a further flavoring agent is selected from the group consisting of, Tulsi oil, Neem oil, Eichinacea tincture, rosemary extracts, goldenseed extracts, passion flower extract, tumeric extracts, betel nut extracts, sunphenon tea extracts, and dandelion root extracts.

8. An organoleptically acceptable oral product containing the composition claimed in claim 6 wherein said flavoring agent is Australian Tea Tree oil, eucalyptol, sage oil or mixtures thereof.

9. Composition claimed in claim 8 wherein Australian Tea Tree oil is present in amounts of about 50 to about 5,000 ppm.

10. Composition claimed in claim 9 comprising about 5 to about 500 ppm each of thymol and eugenol and said composition is a mouthrinse.

11. Composition claimed in claim 9 comprising about 500 to about 3,000 ppm of each of thymol and eugenol and said composition is a toothpaste.

12. A method for preventing the formation of plaque and gingivitis comprising contacting teeth and gums with a composition comprising a combination of thymol and eugenol.

13. A method for preventing the formation of plaque and gingivitis comprising contacting teeth and gums with a composition comprising a combination of thymol, eugenol and a sesquiterpene alcohol.

14. The method claimed in claim 13 wherein the sesquiterpene alcohol is farnesol.

15. The method claimed in claim 12 wherein the composition contains a flavoring agent selected from the group consisting of chamomile, myrhh root, Australian Tea Tree oil, eucalyptol, sage oil and mixtures thereof.

16. The method claimed in claim 15 wherein Australian Tea Tree oil is present.

17. Composition claimed in claim 1 wherein up to about 5% by weight of polyvinyl maleic acid/maleic arthydride copolymer or polyvinyl phosphonate antiplaque activity booster is present.

18. The method claimed in claim 12 wherein said composition contains up to about 5% by weight of polyvinyl maleic acid/maleic anhydride or polyvinyl phosphonate antiplaque activity booster.

19. The method claimed in claim 13 wherein said composition contains up to about 5% by weight of polyvinyl maleic acid/maleic anhydride or polyvinyl phosphonate antiplaque activity booster.

* * * * *